(12) United States Patent
Völzow

(10) Patent No.: US 7,815,647 B2
(45) Date of Patent: Oct. 19, 2010

(54) INTRAMEDULLARY NAIL AND TARGETING INSTRUMENT

(75) Inventor: Stefan Völzow, Mönckeberg (DE)

(73) Assignee: Stryker Trauma GmbH (DE)

( * ) Notice: Subject to any disclaimer, the term of this patent is extended or adjusted under 35 U.S.C. 154(b) by 881 days.

(21) Appl. No.: 10/896,605

(22) Filed: Jul. 22, 2004

(65) Prior Publication Data

US 2005/0203520 A1    Sep. 15, 2005

(30) Foreign Application Priority Data

Jul. 30, 2003    (DE) ................... 203 11 718

(51) Int. Cl.
*A61B 17/58* (2006.01)
*A61B 17/60* (2006.01)
*A61F 2/00* (2006.01)

(52) U.S. Cl. .......................... 606/99; 606/62

(58) Field of Classification Search ............. 606/62–64, 606/96–99, 104; 403/10, 13, 19, 20, 24, 403/292, 347, 359.6, 332, 359.4, 371; 81/44, 81/16, 474, 448

See application file for complete search history.

(56) References Cited

U.S. PATENT DOCUMENTS

| | | | |
|---|---|---|---|
| 5,176,681 A | 1/1993 | Lawes et al. | |
| 5,207,682 A | 5/1993 | Cripe | |
| 5,334,192 A * | 8/1994 | Behrens | 606/96 |
| 5,531,143 A * | 7/1996 | Habermehl et al. | 81/438 |
| 6,302,001 B1 * | 10/2001 | Karle | 81/436 |
| 6,673,076 B2 | 1/2004 | Delogé et al. | |
| 7,077,847 B2 * | 7/2006 | Pusnik et al. | 606/96 |
| 2002/0198534 A1 * | 12/2002 | White et al. | 606/104 |

* cited by examiner

*Primary Examiner*—Thomas C Barrett
*Assistant Examiner*—Andrew Yang
(74) *Attorney, Agent, or Firm*—Lerner, David, Littenberg, Krumholz & Mentlik, LLP

(57) ABSTRACT

An intramedullary nail and targeting and/or nailing instrument are provided, whereby a connection end of the targeting and/or nailing instrument has an axially parallel protrusion and a connection end of the nail has an axially parallel recess in order to couple the targeting and/or nailing instrument. The coupling system couples the targeting/nailing instrument and nail in their rotational position when they contact axially and whereby a connector is also provided in order to connect the targeting and/or nailing instrument and the nail in an axially fixed but also releasable manner. The connection end of the targeting and/or nailing instrument has an end section that engages approximately in one end of the bore-hole section of the nail and the end section and bore-hole section have a deformable element for a releasable snap connection of the parts with the simultaneous contact of the axially parallel protrusion and the axially parallel recess.

15 Claims, 3 Drawing Sheets

INTRAMEDULLARY NAIL AND TARGETING INSTRUMENT

BACKGROUND OF THE INVENTION

The invention relates to a combination of an intramedullary nail and a targeting and/or nailing instrument. More particularly, the invention relates to a spring clip coupling system for connecting the targeting instrument to the nail.

It is known to combine intramedullary bone nails with a nailing instrument in order to drive the nail into the bone channel. For locking nails that are provided with transverse bore holes for driving locking screws, it is also known to simultaneously implement the nailing instrument as the locking screw bore targeting instrument. A targeting instrument serves to locate the transverse bore holes that are not visible in the bone with the locking nail implanted. For this purpose, the targeting instrument, which simultaneously serves as nailing instrument, has, in addition to a connection end with the one end of the nail, a targeting arm that extends approximately parallel and at a distance from the nail. So that the transverse bore holes in the nail can be located, it is required that the nail has a predefined rotational position relative to the targeting and nailing instrument. It is therefore known to provide the end of the nail with one or more axially parallel recesses and the targeting and nailing instrument with one or more axially parallel protrusions. If the protrusion and the recess engage with each other approximately positively, then the approved rotational position is achieved. Furthermore, it is also known to combine the targeting instrument and the nail in an axially fixed manner with each other with the help of a screw. To this end, the hollow end section of the nail has a threaded section and the connection end of the targeting device is provided with an axial screw, which is screwed into the female thread of the nail in order to axially clamp the parts to each other. Such a nail and targeting device is shown in U.S. Pat. No. 5,176,681 and in co-pending U.S. application Ser. No. 10/864,039 filed Jun. 9, 2004.

Before the nail and targeting device are connected or screwed together, conventional systems require that the nail be held in the approved direction against the connection end of the targeting device. To accomplish this, both hands of the user are already engaged. Thus, it is relatively complicated to also execute the described screw connection.

SUMMARY OF THE INVENTION

Thus, one aspect of the invention is to design a combination of an intramedullary nail and targeting and/or nailing instrument such that the connection of both of these parts can be performed by one user.

With the combination according to the invention, the connection end of the targeting and/or nailing instrument has one end section that engages approximately in one end of the bore-hole section of the nail. End section and bore-hole section have means for a releasable snap connection of the parts with the simultaneous engagement of the axially parallel protrusion and axially parallel recess.

The combination according to the invention has the advantage that the second hand of the user, which must normally hold the nail in position, is free in order to screw the parts together.

The snap connection between the nail and the connection end of the targeting and/or nailing instrument only needs to temporarily hold the parts in the approved arrangement with respect to each other until the final fixing takes place via the screw connection. Thus, the snap connection only needs to be implemented such that relatively little power is required to lock together the nail and the connection end of the targeting and/or nailing instrument. This also eases the loosening of the parts if the nail is driven in and the screw is removed from the nail.

According to one embodiment of the invention, the end section of the connection end of the targeting and/or nailing instrument has a radially retreating or deforming section on its perimeter, such as a spring element, that is deformed radially towards the inside when inserting the end section in the bore-hole section of the nail and that works together with a shoulder with sloping sides in the bore-hole section. The connection end of the instrument can therefore be implemented as one piece together with the end section, whereby only degradations or slits can ensure that a radially retreating section is formed. It is to be understood that this has a low excess relative to the diameter of the bore-hole section in the nail, so that the radially retreating section can reach behind a shoulder or recess, if the parts are stuck together. The shoulder can, for example, be formed by a circular groove in the bore-hole section of the nail.

In an alternative embodiment of the invention, the end section of the targeting and/or nailing instrument has a circular groove, in which a circular spring is accommodated such that it is ductile radially towards the inside and stands a bit above the perimeter of the end section in the relaxed state. The end of the bore-hole section has a circular groove, into which the spring expands radially if the end section is inserted into the bore-hole section. The spring is, for example, a slitted circlip.

According to another embodiment of the invention, the circular groove in the end section of the targeting and/or nailing instrument can be interrupted by a partition. This prevents undesired rotation of the circular spring in the groove.

In order to effectively transfer the drive forces to the nail, one embodiment of the invention is designed such that the connection end of the targeting and/or nailing instrument has a radial impact surface that abuts against the free end of the nail, if the releasable snap connection is created.

The coupling system of the present invention for coupling an instrument to a bone nail may include a bone nail which extends along a longitudinal axis and has an end with an internal axial bore. The axial bore includes an axially extending recess formed in a bore wall, the recess being open to the end of the nail. The coupling system includes a connector engaged to the instrument which connector has an end which is insertable into the internal bore for coupling the instrument to the nail end. The connector has an axially extending element, at least part of the element having a radially extent greater than the inner radial extent of the axial recess in the bore. Thus, upon insertion of the connector into the nail bore, the connector element outer surface engages the recess in the nail and locks the connector to the nail at least in the rotational direction.

In addition, either alone or in combination with the axial element and recess, a spring circlip can be utilized to lock the connector and the nail in the axial direction. When the circlip is used, the internal bore includes an annular recess extending radially outwardly of the internal bore diameter into the bore wall in a direction generally perpendicular to the axis of the bone nail. The connector engaged to the instrument then includes the circlip which has an outer diameter slightly larger than the diameter of the internal nail bore so that it is deformed inwardly and then expands into the angular recess in the bone nail bore thereby securely locking the nail and the connector in the axial direction.

BRIEF DESCRIPTION OF THE DRAWINGS

The invention will be explained in greater detail below with reference to an embodiment example represented in drawings.

DETAILED DESCRIPTION

Figure 1:
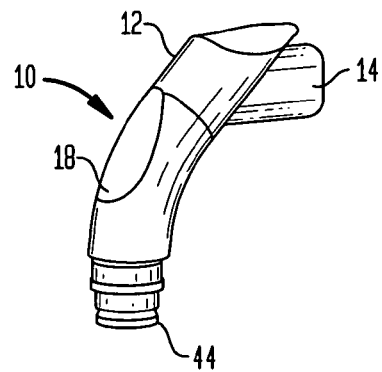
FIG. 1 shows a perspective view of the connection end of a targeting and/or nailing instrument according to the invention.

FIG. 1 shows a connection end 10 of a targeting and/or nailing instrument that comprises an actual connection piece 12 and a part 14 (not described in further detail here) which serves to create a connection with the cross-bore targeting part of the targeting and nailing instrument, which is not shown in detail and is also well known.

Figure 3:
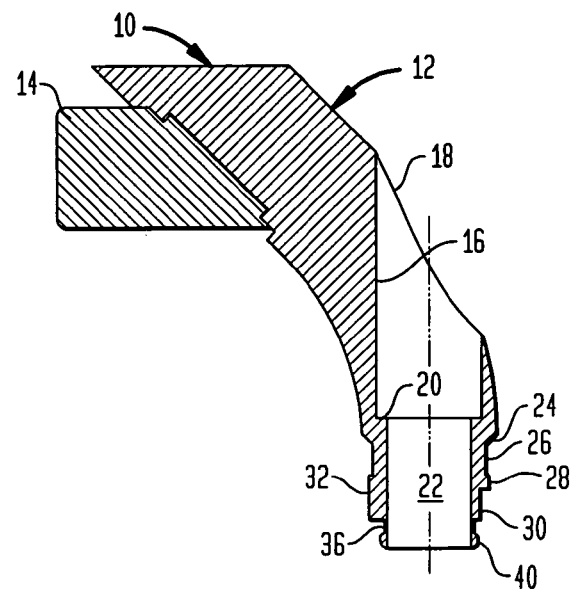
FIG. 3 shows a cross-section through the illustration according to FIG. 3 along the line 3-3.
Figure 4:
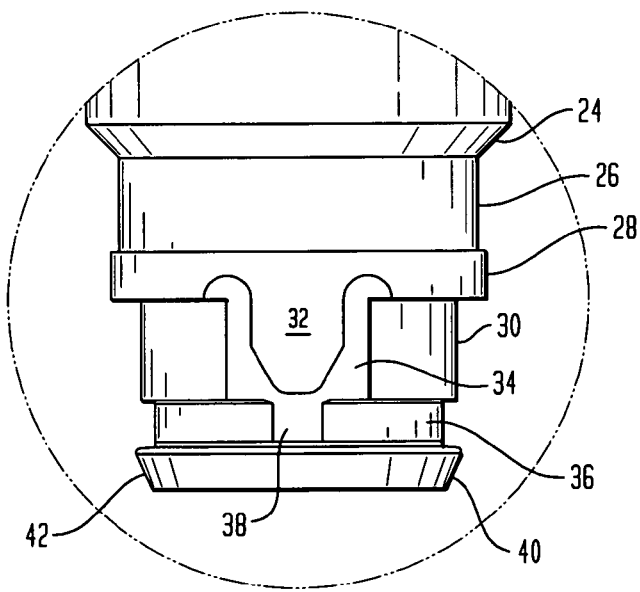
FIG. 4 shows an enlarged view of circle portion 4 FIG. 3.

As can be seen from FIGS. 3 and 4, the connection piece 12 of the preferred embodiment has a straight bore hole 16 that ends on the upper end in a sloped oval opening 18. An annular ring shoulder 20 is formed within the bore hole 16. A bore-hole section 22 with a constant diameter is provided below annular shoulder 20. A conical or tapered step 24 is located on the exterior side of the circular, cross-sectional section of the connection part below annular shoulder 20 and a first cylindrical section 26, below which a second cylindrical section 28 with a slightly larger diameter connects. Another cylindrical section 30 with a smaller diameter is provided below the cylindrical section 28, but is only partially cylindrical, because it is interrupted on the side which faces part 14 by an axially extending radial protrusion 32. This protrusion 32 can be best seen in FIG. 4. Protrusion 32 has an external diameter equal to the diameter of cylindrical section 28 and thus extends beyond (stands above) section 30, which in the area 34 adjacent protrusion 32 is flattened on both sides of the protrusion 32, so that the protrusion 32 is raised sufficiently radially outwardly.

A radial groove 36 is formed below the cylindrical section 30, which is interrupted by an axially parallel partition 38. A conical section 40 is provided below the radial groove 36, the exterior surface 42 of which tapers inwardly downward. The radial groove 36 serves to accept a slitted circlip or snap ring, whereby the ends of the spring circlip lie on both sides of the partition 38 (not shown) at a short distance from it. This type of spring is implied by dark line 44 in FIG. 1 and shown in detail in FIGS. 8 and 9 as circlip 80

Figure 5:
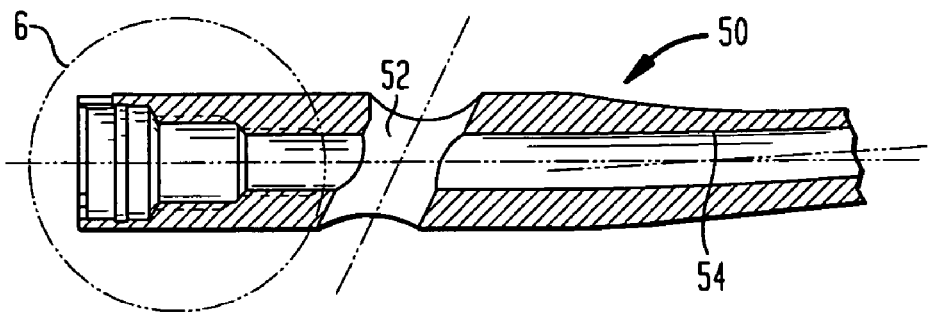
FIG. 5 shows a cross-section through a femur nail for the treatment of trochanter or femoral neck fractures.
Figure 6:
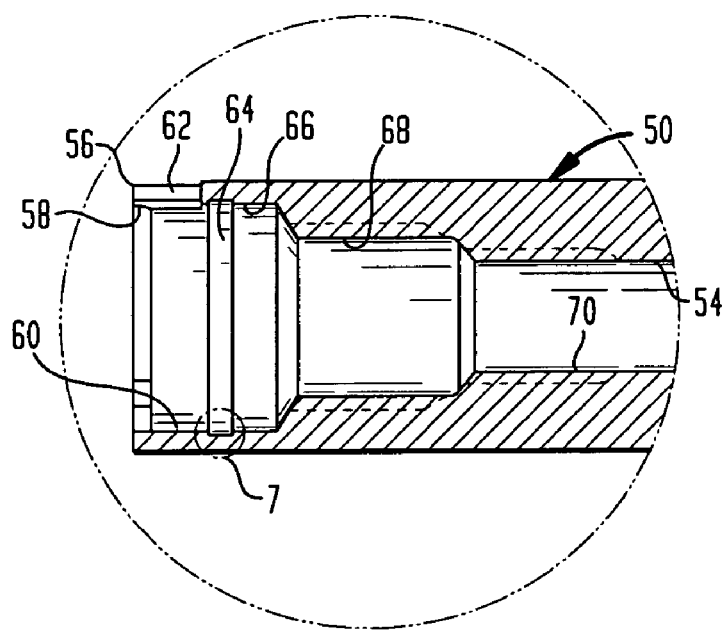
FIG. 6 shows an enlarged view circle portion 6 of FIG. 5.

FIGS. 5 and 6 show a cross-section of a proximal end section 50 of a not-further-described femur nail, which has a slanted bore hole 52 for the acceptance of a femoral neck screw that is also not shown. The nail has an axial bore hole 54. The other parts of end section 50 are explained using FIG. 6.

Figure 7:
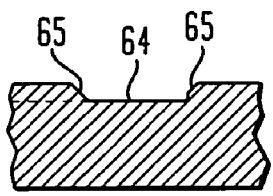
FIG. 7 shows an enlarged view of circled portion 7 of FIG. 6.

The nail has a free face surface 56, to which a conical inwardly tapered insertion section 58 connects. A cylindrical internal bore-hole section 60 connects to section 58. The wall of the nail in section 60 has an axially parallel recess 62 in the area of the bore-hole section 60 and the insertion section 58. Recess 62 is open to face 56 and is sized to receive protrusion 32. A circular groove 64 connects to the bore-hole section 60 which, in turn, connects with a cylindrical bore-hole section 66 with a somewhat smaller diameter than groove 64. The groove 64 is more clearly shown in FIG. 7. It can be seen that the end walls 65 of groove 64 are slanted.

A first female thread section 68 lies further from the end of the nail and this is followed by a second thread section 70 with a smaller diameter.

Figure 2:
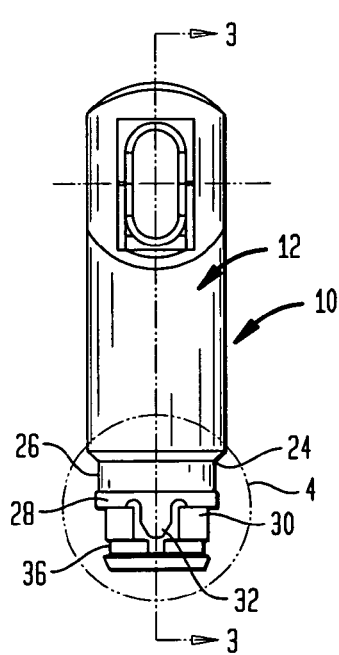
FIG. 2 shows a side view of the connection end according to FIG. 1.

The largest external diameter of section 40 (FIG. 4) corresponds approximately to the internal diameter of the bore-hole section 60, which is equal to the internal diameter of the bore-hole section 66. The end section of connection part 12 illustrated in FIGS. 2 through 4 can therefore be inserted into the bore-hole sections 60 and 66 if the axially parallel, nose-like protrusion 32 is aligned with the recess 62. Both of these sections engage approximately with each other. The conical insertion section 58 and the conical section 40 of the end section ease this coupling together. The insertion of the end section of the connection part 12 ends when the shoulder surface of cylindrical section 28, which is turned towards the nail, hits the end surface 56 of the nail. When this occurs, then groove 36 on the connection part 12 and groove 64 of nail 50 are aligned and located across from each other. If the already mentioned circlip 80, which has a certain radial excess with respect to the diameter of the bore-hole section 60 which allows the circlip to deform radially inwardly, is now located in groove 36, then the circlip 48 snaps outwardly into the groove 64, thereby axially fixing the two parts together. The nail 50 is therefore connected in the rotational direction by protrusion 32 and slotted recess 62 and axially by circlip 80 in the correct position with the connection end 10 of the targeting and/or nailing instrument. Henceforth, the secure connection of these two parts can be made by a screw or a screw sleeve. After driving the nail into the bone channel and loosening the screw connection, the instrument can be loosened from the nail with little force as slanted end wall 65 deforms the circlip 80 radially inwardly. It is to be understood that a sleeve can be used as the screw, which is fed through the bore hole 16 (FIG. 3) and works together with the thread section 68 of the nail, as is described, for example, in U.S. Pat. No. 5,176,681. The screw works together with the thread section 68 of the nail. A locking pin (not shown) can work together with the thread section 70 of the nail 50 in order to determine the rotational position in the desired manner a (not shown) femoral neck screw, which is fed through the transverse bore hole 52.

Figure 8:
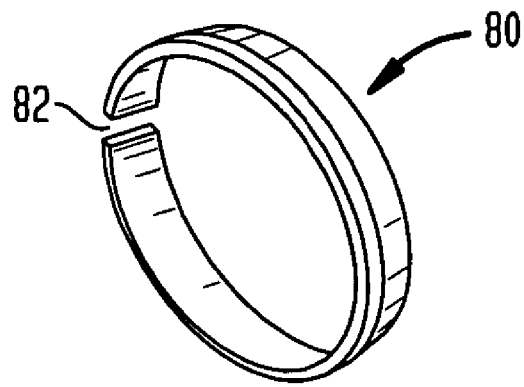
FIG. 8 is an isometric view of the clip of the present invention.
Figure 9:
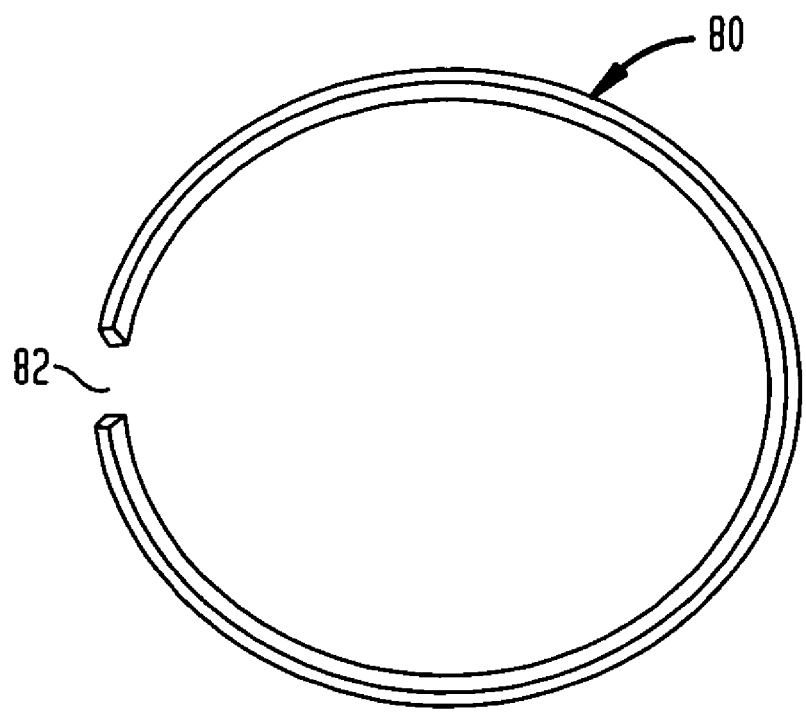
FIG. 9 is a bottom view of the clip of FIG. 8.

FIGS. 8 and 9 show the preferred spring clip or circlip of the present invention generally denoted as 80. Clip 80 is mounted in groove 36 and includes slit 82 which allows clip 80 to deform inwardly on insertion into bore hole section 60 and then expand into groove 64 upon full assembly of connection end 10 and nail end 50. Slanted or shaped portions 65 are angled inwardly towards the internal nail bore and aid in the disassembly of connector 10 and nail 50.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A coupling system for coupling an instrument to a bone nail comprising:
   a bone nail extending along a longitudinal axis and having an end with an internal axial circular bore having a first diameter including an axially extending recess formed in a wall of said bore, said recess open to said nail end and a groove intermediate ends of the internal axial bore having a diameter greater than the first diameter; and
   a connector engaged to the instrument and having an end insertable into the internal bore for coupling the instrument to said nail end, said end of said connector having an inwardly deformable spring element, at least a part of said spring element having a diameter greater than the first diameter of said bore when in a relaxed state for extending into the groove, the connector having a protrusion with an outwardly facing surface bounded by radially inwardly extending side surfaces for engaging the recess in the nail, the protrusion spaced further from the end of the connector insertable into the nail bore than the spring element, the protrusion has recessed areas adjacent the side surfaces thereof which recessed areas are flattened in a plane facing in the same direction as the outwardly facing surface to raise the protrusion radially outwardly.

2. A coupling system for coupling an instrument to a bone nail, the system comprising:
   a bone nail extending along a longitudinal axis and having an end with a circular internal bore including an annular recess formed intermediate ends of the bore and a recess extending parallel to the longitudinal axis of the nail open to an outer end surface of the nail extending radially outwardly of a diameter of said internal bore in a direction generally perpendicular to said axis;
   a connector on the instrument having an end and insertable into said internal bore for coupling the instrument to the nail end, said connector having a radially inwardly deformable spring element mounted thereon for engaging the recess in said nail bore, the spring element adjacent the instrument end extending beyond an outer perimeter of the connector when in a relaxed state;
   the connector including an axially parallel protrusion spaced further from the instrument end than the spring and insertable in the bone nail recess wherein the axially parallel protrusion engageable with an axially extending recess in the internal bore of said nail and has an outwardly facing surface bounded by radially inwardly extending side surfaces and has recessed areas adjacent the side surfaces facing in the same direction as the outwardly facing surface;
   wherein the spring element has a rectangular cross section; and
   wherein an end wall of the groove is slanted for deforming the spring element radially inwardly when disassembling the instrument from the nail.

3. The coupling system as set forth in claim 2 wherein said recess in said internal nail bore is a circumferential groove.

4. The coupling system as set forth in claim 3 wherein said inwardly deformable spring element is a circlip.

5. The coupling system as set forth in claim 3 wherein said circlip is slitted.

6. The coupling system as set forth in claim 4 wherein said circlip is mounted in an outwardly facing circumferential groove on said connector and can deform radially inwardly into said groove at or below the perimeter of the connector on engaging said nail internal bore and expand into said circumferential nail groove upon full insertion of said connecter into said nail bore.

7. The coupling system as set forth in claim 6 wherein said circumferential nail groove has a central portion extending parallel to said longitudinal axis and end portions extending from said central portion towards said internal bore at an angle to said axis.

8. The coupling system as set forth in claim 2 wherein said connector and said nail include engageable elements for preventing rotation between said nail and said connector about said axis.

9. A combination comprising an intramedullary nail and a targeting and/or nailing instrument, a connection end of the targeting and/or nailing instrument having an axially parallel protrusion and a connection end of the nail having a bore hole section and an axially parallel recess in order to fix together the targeting and/or nailing instrument and nail in their rotational position when they contact axially and whereby a means for connecting the nail and targeting and/or nailing instrument are also provided in order to connect the targeting and/or nailing instrument and the nail in an axially fixed but also releasable manner, wherein the connection end of the targeting and/or nailing instrument has an end section that engages in one end of the bore-hole section of the connection end of the nail by means of a releasable snap connection of the parts with the simultaneous contact of axially parallel protrusion and axially parallel recess;
   wherein the end of the bore-hole section of the connection end of the nail has a circular groove, in which a spring element of the snap connection expands radially if the end section of the connection end of the targeting and/or nailing instrument is inserted into the bore-hole section of the connection end of the nail;
   wherein the spring element has a rectangular cross section;
   wherein an end wall of the circular groove is slanted for deforming the spring element radially inwardly when disassembling the instrument from the nail; and
   wherein the axially parallel protrusion at the connection end of the targeting and/or nailing instrument has an outwardly facing surface bounded by radially inwardly extending side surfaces and has recessed areas adjacent the side surfaces facing in the same direction as the outwardly facing surface.

10. The combination as set forth in claim 9, wherein the end section of the connection end of the targeting and/or nailing instrument has a radially retreating section on its perimeter that is deformed radially towards the inside when inserting the end section of the connection end of the targeting and/or nailing instrument into the bore-hole section of the connection end of the nail and that works together with a shoulder having sloped sides in the bore-hole section.

11. The combination as set forth in claim 10, wherein the bore-hole section of the connection end of the nail has a radial groove, into which the radially retreating section of the connection end of the targeting and/or nailing instrument engages.

12. The combination as set forth in claim 9, wherein the end section of the connection end of the targeting and/or nailing instrument has a circular groove, in which a circlip is accepted such that it is deflectable towards the inside and stands a bit above a perimeter of the end section of the connection end of the targeting and/or nailing instrument in the relaxed state, the circlip expands radially into the circular groove when the end section of the connection end of the targeting and/or nailing instrument is inserted into the bore-hole section of the connection end of the nail.

13. The combination as set forth in claim 12, wherein a slitted circlip is provided.

14. The combination as set forth in claim 12, wherein the circular groove in the end section of the connection end of the targeting and/or nailing instrument is interrupted by a partition.

15. The combination according to claim 9, wherein the connection end of the targeting and/or nailing instrument has a radial impact surface, against which a free end of the connection end of the nail abuts when the releasable snap connection is created.

* * * * *

UNITED STATES PATENT AND TRADEMARK OFFICE
CERTIFICATE OF CORRECTION

Page 1 of 1

PATENT NO.         : 7,815,647 B2
APPLICATION NO.    : 10/896605
DATED              : October 19, 2010
INVENTOR(S)        : Stefan Völzow It is certified that error appears in the above-identified patent and that said Letters Patent is hereby corrected as shown below:

Cover Page, under [57] Abstract, line 2, "are provided" should read --is provided--.
Column 1, line 18, "serves as nailing" should read --serves as the nailing--.
Column 1, line 36, "device is shown" should read --device are shown--.
Column 3, line 4, "represented in draw-" should read --represented in the draw- --.
Column 3, line 12, "according to FIG. 3" should read --according to FIG. 2--.
Column 3, line 13, "portion 4 FIG. 3" should read --portion 4 of FIG. 2--.
Column 3, line 16, "view circle portion 6" should read --view of circle portion 6--.
Column 3, line 59, "80" should read --80.--.

Signed and Sealed this
Twenty-second Day of November, 2011

David J. Kappos
*Director of the United States Patent and Trademark Office*